United States Patent [19]

Roche

[11] Patent Number: 4,643,202
[45] Date of Patent: Feb. 17, 1987

[54] MULTI-MATERIAL INSULATION SHEATH FOR PACER LEAD

[75] Inventor: Thomas J. Roche, North Lauderdale, Fla.

[73] Assignee: Cordis Corporation, Miami, Fla.

[21] Appl. No.: 723,163

[22] Filed: Apr. 15, 1985

[51] Int. Cl.⁴ ............................................. A61N 1/04
[52] U.S. Cl. ................................. 128/786; 128/419 P
[58] Field of Search ..................... 128/419 P, 784–786

[56] References Cited

U.S. PATENT DOCUMENTS

| | | | |
|---|---|---|---|
| 3,367,339 | 2/1968 | Sessions | 128/786 |
| 4,012,103 | 5/1977 | Lundquist | 128/419 P |
| 4,414,986 | 11/1983 | Dick | 128/786 |

Primary Examiner—William E. Kamm
Attorney, Agent, or Firm—George H. Gerstman

[57] ABSTRACT

An insulated electrical lead has a first section of insulation extending along the lead which is made of a first material and a second section of insulation extending along the lead which is made of a second material. The second material is softer and less stiff than the first material.

10 Claims, 6 Drawing Figures

MULTI-MATERIAL INSULATION SHEATH FOR PACER LEAD

BACKGROUND OF THE INVENTION

Cardiac pacers are used for regulating heart beats in patients who suffer from a failure of the natural regulatory system. The cardiac pacer includes one or more electrodes carried on leads which are enclosed in an insulating sheath, with the one or more electrodes communicating with the exterior so that they can be in contact with the heart.

Typically, cardiac pacers are designed for entry through a vein to the ventricle of the heart (pervenous) or, alternatively, the cardiac pacer may be sutured onto the ventricle of the heart (myocardial).

Insulated sheaths of cardiac pacers which are currently available may be made of silicone elastomer, polyurethane, or polytetrafluoroethylene (Teflon). Polyurethanes are particularly growing in favor for use as insulation for an electrical lead because of its strength and flexibility. This for example makes possible the placement of two pervenous leads into one vein since the polyurethane insulation can be thinner because of its higher strength. It has been particularly desirable to use harder grades of polyurethane as an insulating sheath (a Shore D hardness of about 55 or more).

However, this relatively stiff insulation, while having advantage due to its high biological stability, is considered by many to be too stiff for safe use within the atrium or ventricle of the heart, even when thin-walled insulation is used so that the lead has a diameter of only about 2 millimeters. There is a concern that while it is desired for portions of the cardiac pacer lead which are remote from the heart to have stiff insulation, there is a risk that stiff insulation in the immediate vicinity of the heart can damage the heart tissue as the heart beats.

Accordingly, while it would be desirable to use stiff polyurethane formulations in a cardiac pacer lead for advantages in placement of the lead in blood vessels and the like, there is a major potential disadvantage in the use of a cardiac pacer having stiff insulation in that it may damage the heart.

By this invention it becomes possible to make use of the desirable stiff insulating material in electrical leads and particularly cardiac pacer leads to achieve the advantages resulting therefrom, while at the same time providing protection to the heart from damage due to the stiff insulation.

DESCRIPTION OF THE INVENTION

In accordance with this invention, an insulated electrical lead is provided, typically for use in a cardiac pacing system. A first section of insulation extends along the lead, being made of a first material, while a second section of insulation extends along the lead, being made of a second material. The second material is softer and less stiff than the first material. When the lead of this invention is used as part of a cardiac pacer, it typically includes at least one external electrode positioned adjacent to the second section of insulation. Preferably one electrode is positioned at one end of the second section, while, if desired, other electrodes may be interspersed throughout the second section.

At least one electrical lead wire, communicating with the electrode, is positioned within the insulation. The electrical lead wire may extend straight through the insulation if desired, but typically and preferably the lead wire is positioned within the insulation in helical arrangement. A plurality of lead wires may also be found within the insulation communicating with separate electrodes when multiple electrodes are present.

The first material preferably has a Shore D durometer of at least 50 and preferably at least 55. The first material may desirably be a polyurethane formulation of this degree of stiffness.

The second material may be a silicone elastomer formulation which is relatively soft when compared with the first material. The second section of insulation which comprises the second material may carry one or more of the electrodes and may be positionable within or adjacent to the heart to permit the electrodes to be in contact with the necessary section of the heart. Accordingly, as the heart beats, no damage takes place to the heart tissue because of the soft silicone elastomer found in the second section of insulation. Nevertheless, the first section of insulation, which typically occupies portions of the electrical lead which are remote from the heart, may be stiff, providing the desired advantages of stiffness to the heart pacer lead using the invention of this application. Typically, the second material may have a Shore A hardness of about 80.

Typically, the second section of insulation comprising the softer material may be several centimeters in length, up to, for example, 15 centimeters. The remainder of the electrical lead may be sheathed with the first section of insulation, which also may extend from about 1 to 15 centimeters, for example, or longer.

There is a further advantage of this invention. When a pair of cardiac pacing leads are inserted through the same vein, the desired, relatively stiff insulating sheath of the leads may have a smaller diameter, particularly when made of a strong, thin polyurethane sheath, and may have a low coefficient of friction. The relatively stiff portion of the insulation thus can facilitate insertion of the second cardiac pacing lead.

Additionally, certain cardiac pacing leads are designed to be fixed into the cardiac muscle by means of a screw carried on the distal end of the lead, relative to the heart. In such leads, a torque-transmitting sheath is required. In this instance, the relatively stiff insulation portion used in this invention provides advantage, in that it transmits torque much more effectively than a pacer in which its lead is insulated along its entire length with a soft insulation such as silicone elastomer. Nevertheless, as stated above, the heart tissue is protected by the use of a second section of insulation of soft, biocompatible material such as silicone elastomer.

DESCRIPTION OF SPECIFIC EMBODIMENTS

Figure 1:
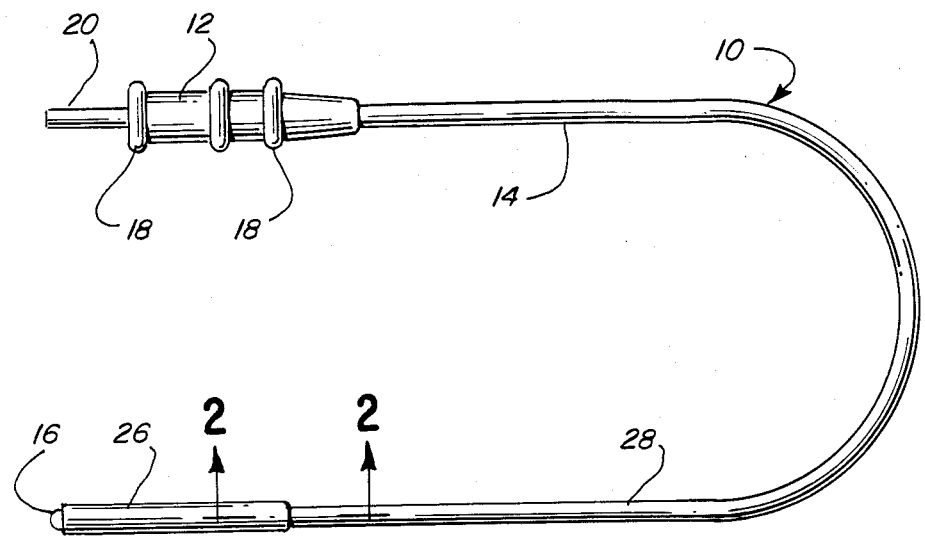
FIG. 1 is an elevational view of a pervenous cardiac pacing lead made in accordance with this invention.
Figure 2:
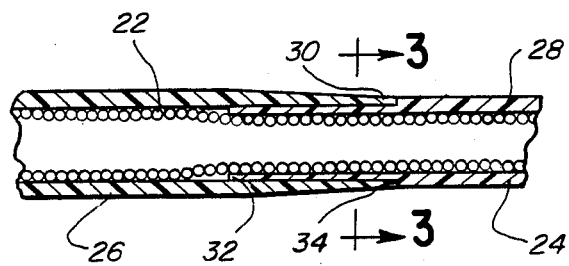
FIG. 2 is a longitudinal section taken along line 2—2 of FIG. 1.
Figure 3:
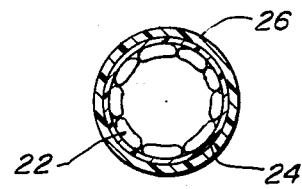
FIG. 3 is a cross section taken along line 3—3 of FIG. 2.

Referring to FIGS. 1 through 3, a pervenous monopolar cardiac pacing lead 10 is disclosed. Lead 10 is of generally conventional design except for the use of the invention of this application. Cardiac pacing lead includes a pacer lead assembly 12, an insulated lead wire 14 and distal electrode 16. Coiled lead wire 22 is shown in FIGS. 2 and 3 to be helically arranged inside the tubular insulation 24 of the lead. Lead wire 22 communicates between electrode 16 and terminal pin 20.

Lead 10 may have flanges, wings, tines or fins, if desired, in the vicinity of electrode 16, attached to and extending lateral to the body 14 of the lead. Pacer terminal assembly 12 may carry ring seals 18 to abut the interior wall of a pacer lead connector, to prevent fluid intrusion into the pacer neck. At the same time, terminal pin 20 enters into contact with the same pacer lead connector.

The distal fifteen centimeters of insulating sheath 24, adjacent to electrode 16, may constitute the second section of insulation 26, and may be made of a soft, flexible silicone elastomer. The remaining portion 28 of the sheath may constitute the first section of insulation, extending to pacer lead connector 12. First section 28 of the sheath may have a Shore D hardness of about 55 and may be a polyurethane material, for example Pelethane D 55 sold by Upjohn of Kalamazoo, Mich. Accordingly, the rear portion of pacing lead 10 may be relatively stiff for ease of control and the other advantages specified above, while the forward portion 26 of the insulation may be soft and pliable to permit contact with the heart without damaging any tissue as the heart beats.

Referring particularly to FIGS. 2 and 3, the junction area between first section 28 and second section 26 is shown. The end 30 of silicone elastomer section 26 is tapered or feathered as shown to a relatively thin and annular end. At the same time the end 32 of first section 28 is fabricated to be of reduced outer diameter, so as to receive end 30 in telescoping relation. Annular step 34 is also provided in first, polyurethane section 28 to receive silicone rubber annular section 26 in abutting relation. Sections 26, 28 may be sealed together using any desired medical grade adhesive so that a smooth transitional surface is provided between the two sections 26, 28. Specifically, the medical adhesive used may be Dow Corning medical adhesive.

Figure 4:
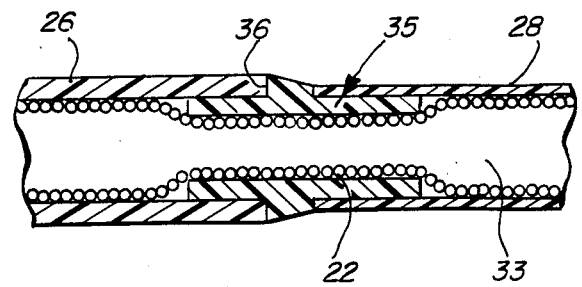
FIGS. 4, 5 and 6 are each fragmentary longitudinal sections of separate alternative embodiments for a cardiac pacing lead that would otherwise be similar to the lead of FIG. 1, the sections being taken along lines equivalent to line 2—2 of FIG. 1.

Referring to FIG. 4, a modification is shown in the means for connecting first and second sections of insulation 26, 28. It is to be understood that the coiled electrical conductor 22 passes through the bore 33 defined by the insulation, though only part is shown.

A preformed tube 35, defining annular ledge 36, is positioned between sections of insulation 26, 28, with sections of insulation 26, 28 being bonded to tubular member 35 by means of any desired medical grade adhesive. Tube 35 may be made of polyethersulfone, or any other desired material.

Annular projection 36 provides a transition area between the second silicone rubber section 26 and first polyurethane section 28 to account for the difference in their thickness as shown. Accordingly, the softer silicone section 26 may have a significantly greater thickness than the thinner, stiffer, and stronger polyurethane section 28.

Figure 5:
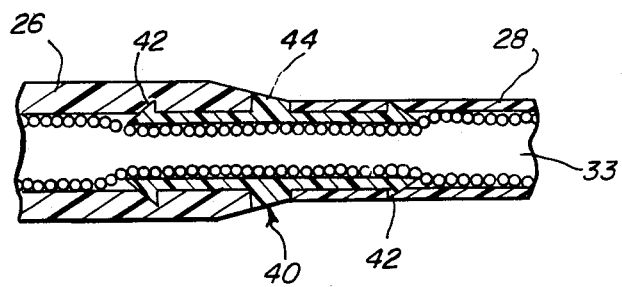

Turning to FIG. 5, another design of tubular connector 40 is shown for connecting the two sections 26, 28. In this instance, tubular member 40 may have an annular barb 42 on each end to assist in the retention of sections 26, 28, although medical grade adhesive may be used to strengthen the connection as desired.

Central annular projection 44 is provided to tube 40, being proportioned to prevent the ends of sections 26, 28, from forming undesirable projecting edges at their connection. Tubular member 40 may be made of polyethersulfone or any other desired material as in the previous embodiment.

Figure 6:
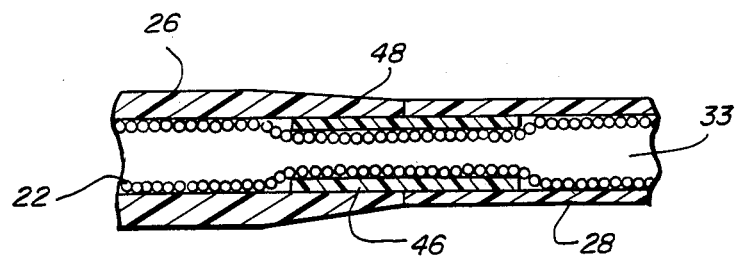

Referring to FIG. 6, insulating sections 26, 28, are brought together in abutting relation with the thicker silicone section 26, being feathered at area 48 to avoid the undesirable projecting edges at its junction point with section 28.

Internal tubular sheath 46 may be bonded to both sections 26, 28 with appropriate medical grade adhesive to strengthen the junction.

One or more helically arranged electrical conductors 22 will be coiled inside of the leads shown in the embodiments of FIGS. 4 through 6. Alternatively, straight conductors or the like may be used as a substitute for the coiled electrical lead wire 22. The bore 33 of each lead may be proportioned to receive a stylet to facilitate insertion.

Tubular member 46 may be made from the same materials as tubular members 35 and 40.

If desired, a bipolar or multipolar cardiac pacing lead may be constructed in accordance with the principles of this invention, so that the distal few centimeters of the lead insulation are made of a relatively soft material, while the remainder of the lead insulation is made of a stiffer material. Also, separated sections of soft material may be placed along the length of an electrical lead made in accordance with this invention, being separated by sections of harder insulation. Typically the electrodes will project out from the softer section areas.

It is also contemplated that the cardiac pacing lead of this invention is not only usable in the pervenous form, but also for myocardial implantation on an external surface of the heart.

The invention of this application may be applied to other electrical leads, particularly those which transmit electrical stimuli to a tissue site other than the heart which requires electrical stimulation.

The above has been offered for illustrative purposes only, and is not intended to limit the scope of the invention of this application, which is as defined in the claims below.

That which is claimed is:

1. In an insulated electrical lead having a proximal end, a distal end, an electrical conductor extending from the proximal end to the distal end and having insulation covering the conductor along the lead, a portion of the conductor at the distal end being free of insulation with the distal end being adapted for implantation and contact of the free portion of the conductor with the tissue of the patient, the improvement comprising, in combination:

said insulation comprising a first section of insulation and a second section of insulation occupying a different portion of the lead than said first section of insulation, said first section of insulation extending along most of the lead and said second, different section of insulation being located at the distal end of the lead, said first section of insulation being harder and stiffer than said second section of insulation, whereby the first section of insulation has the ability to transmit torque more effectively than the second section but the patient's tissue is protected by the softer, second section of insulation.

2. The insulated lead of claim 1 in which said first section comprises a polyurethane formulation having a Shore D durometer of at least 50.

3. The insulated lead of claim 1 in which said second section comprises a silicone elastomer formulation.

4. The insulated lead of claim 1 in which said first and second sections of insulation overlap each other in telescoping bonded relation in a junction area between them.

5. The insulated lead of claim 1 in which a tubular junction member is carried on said lead between the first and second sections, said first and second sections each overlapping opposed ends of said tubular junction member in telescoping, bonded relation thereto.

6. The insulated lead of claim 5 in which said tubular junction member is made of polyethersulfone.

7. The insulated lead of claim 1 which includes at least one external electrode positioned at one the distal of the second section.

8. In an insulated electrical lead having a proximal end, a distal end, an electrical conductor extending from the proximal end to the distal end and having insulation covering the conductor along the lead, a portion of the conductor at the distal end being free of insulation with the distal end being adapted for implantation and contact of the free portion of the conductor with the tissue of the patient, the improvement comprising, in combination:

said insulation comprising a first section of insulation and a second section of insulation occupying a different portion of the lead than said first section of insulation, said first and second sections of insulation overlapping in telescoping bonded relationship in a junction area between them, said first section of insulation extending along most of the lead and said second, different section of insulation being located at the distal end of the lead, said first section of insulation comprising a polyurethane formulation having a Shore D durometer of at least 50 and being harder and stiffer than said second section of insulation, said second section of insulation comprising a silicon elastomer formulation, whereby the first section of insulation has the ability to transmit torque more effectively than the second section but the patient's tissue is protected by the softer, second section of insulation; and at least one electrical lead wire being positioned within said insulation in helical arrangement.

9. In an insulated electrical lead as described in claim 8, in which a tubular junction member is carried on said lead between the first and second sections, said first and second sections each overlapping opposed ends of said tubular junction member in telescoping, bonded relation thereto.

10. In an insulated electrical lead as described in claim 9, in which said tubular junction member is made of polyethersulfone.

* * * * *